United States Patent
Jolma et al.

(10) Patent No.: US 12,267,577 B2
(45) Date of Patent: Apr. 1, 2025

(54) APPARATUS AND METHOD FOR IMAGING FUNDUS OF EYE

(71) Applicant: Optomed Plc, Oulu (FI)

(72) Inventors: Ilkka Jolma, Oulu (FI); Kenneth Oksanen, Oulu (FI); Juho Pylvänäinen, Oulu (FI)

(73) Assignee: Optomed Plc, Oulu (FI)

( * ) Notice: Subject to any disclaimer, the term of this patent is extended or adjusted under 35 U.S.C. 154(b) by 186 days.

(21) Appl. No.: 17/986,525

(22) Filed: Nov. 14, 2022

(65) Prior Publication Data
US 2023/0156320 A1 May 18, 2023

(30) Foreign Application Priority Data
Nov. 16, 2021 (EP) .................... 21208395

(51) Int. Cl.
| | |
|---|---|
| *H04N 23/60* | (2023.01) |
| *A61B 3/00* | (2006.01) |
| *A61B 3/12* | (2006.01) |
| *A61B 3/14* | (2006.01) |
| *H04N 23/611* | (2023.01) |
| *H04N 23/63* | (2023.01) |

(52) U.S. Cl.
CPC .......... *H04N 23/64* (2023.01); *A61B 3/0008* (2013.01); *A61B 3/12* (2013.01); *A61B 3/145* (2013.01); *H04N 23/611* (2023.01); *H04N 23/635* (2023.01)

(58) Field of Classification Search
CPC .... H04N 23/64; H04N 23/635; H04N 23/611; A61B 3/0008; A61B 3/12
See application file for complete search history.

(56) References Cited

U.S. PATENT DOCUMENTS

| | | |
|---|---|---|
| 2014/0132928 A1 | 5/2014 | Ono |
| 2018/0336679 A1 | 11/2018 | Farchione et al. |
| 2019/0357769 A1 | 11/2019 | Wang |

FOREIGN PATENT DOCUMENTS

JP  2007-202724  8/2007

OTHER PUBLICATIONS

Chander Dev, et al., "Diagnostic Quality Assessment of Ocular Fundus Photographs: Efficacy of Structure-Preserving ScatNet Features", 2019 $41^{ST}$ Annual International Conference of the IEEE Engineering in Medicine and Biology Society (EMBC), IEEE, Jul. 23, 2019, pp. 2091-2094 (4 pages).

(Continued)

*Primary Examiner* — On S Mung
(74) *Attorney, Agent, or Firm* — Nixon & Vanderhye PC

(57) ABSTRACT

Apparatus and method for imaging fundus of eye. The apparatus (100) includes an optical system (116), an image sensor (114) to capture a still image or a video through the optical system (116), a user interface (102) including a display (104) to display data to a user of the apparatus, and one or more processors (106). The one or more processors (106) cause performance of at least the following: setting the image sensor (114) to capture an aiming video; detecting a retina of the eye in the aiming video; setting the display (104) to display the aiming video with a highlight of the detected retina; and setting the image sensor (114) to capture one or more final still images of the fundus or a final video of the fundus.

20 Claims, 5 Drawing Sheets

(56) References Cited

OTHER PUBLICATIONS

Figure 1:
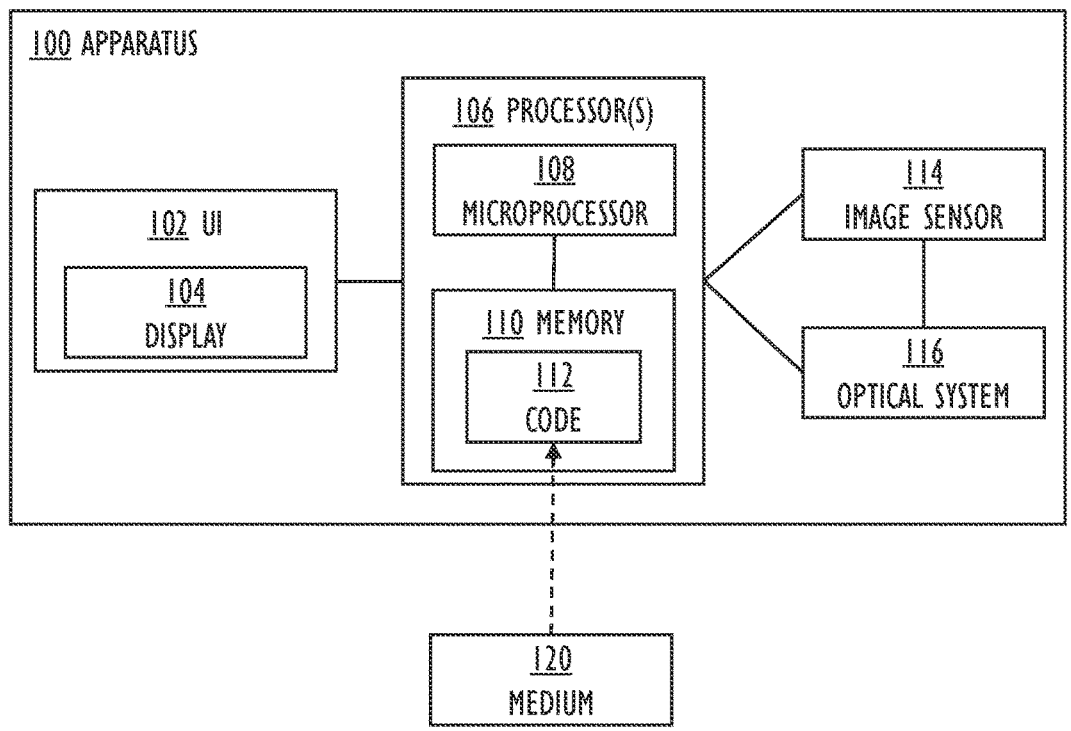

Muhammad Moazam Fraz, et al., "An Ensemble Classification-Based Approach Applied to Retinal Blood Vessel Segmentation", IEEE Transactions on Biomedical Engineering, IEEE, vol. 59, No. 9, Sep. 1, 2012, pp. 2538-2548 (11 pages).
Extended European Search Report for EP Application No. 20218395.0 dated May 6, 2022, 10 pages.

APPARATUS AND METHOD FOR IMAGING FUNDUS OF EYE

CROSS-REFERENCE TO RELATED APPLICATIONS

This application claims priority to EP patent application Ser. No. 21/208,395.0, filed Nov. 16, 2021, the entire contents of which are hereby incorporated by reference.

FIELD

Various embodiments relate to an apparatus for imaging a fundus of an eye, and to a method for imaging the fundus of the eye.

BACKGROUND

The fundus of the eye is the rear interior surface of the eye opposite the lens. The fundus comprises the retina, optic disc (or optic nerve head), macula (or macula lutea), fovea, and posterior pole. Traditionally, the fundus is examined by ophthalmoscopy, but nowadays fundus photography is also used. With the fundus photography, the central and peripheral retina, optic disc, and macula may be examined. The applicant, medical technology company Optomed, is the leading manufacturer of handheld fundus cameras globally. Optomed Aurora® IQ is an example of a handheld fundus camera. Although it is easy to use, correct operation and practice is required especially in aiming the camera correctly to capture a still image or a video of the fundus.

BRIEF DESCRIPTION

According to an aspect, there is provided an apparatus for imaging a fundus of an eye comprising: an optical system; an image sensor to capture a still image or a video through the optical system; a user interface including a display to display data to a user of the apparatus; one or more processors to cause performance of at least the following: setting the image sensor to capture an aiming video; detecting a retina of the eye in the aiming video; setting the display to display the aiming video with a highlight of the detected retina; and setting the image sensor to capture one or more final still images of the fundus or a final video of the fundus.

According to an aspect, there is provided a method for imaging a fundus of an eye comprising: setting an image sensor to capture an aiming video through an optical system; detecting a retina of the eye in the aiming video; setting a display to display the aiming video with a highlight of the detected retina; and setting the image sensor to capture one or more final still images of the fundus or a final video of the fundus through the optical system.

In an embodiment, the one or more processors cause performance of detecting the retina comprises using a machine vision algorithm trained with images of eyes with annotated fundi.

In an embodiment, the one or more processors cause performance of detecting the retina comprises using an Adaptive Boosting, AdaBoost, statistical classification meta-algorithm or one of its variants, which construct a strong classifier by combining results of a sequence of weak classifiers.

In an embodiment, the one or more processors cause performance of determining, by the weak classifiers, a probability of a pixel of interest in a single frame of the aiming video belonging to the retina by comparing either an average luminosity of an area in the single frame relative to the pixel of interest to a first constant, or a difference of averages of luminosities of two areas in the single frame relative to the pixel of interest to a second constant.

In an embodiment, the one or more processors cause performance of using, by the weak classifiers, also one or more results of comparisons from previous weak classifiers in the sequence of the classifiers to improve the accuracy of a next weak classifier in the sequence of the classifiers.

In an embodiment, the one or more processors cause performance of comparing, by the weak classifiers, also average probabilities of pixels in areas in the single frame belonging to the retina as determined by an already executed weak classifier as follows: comparing either an average probability of an area in the single frame relative to the pixel of interest to a third constant, or a difference of averages of probabilities of two areas in the single frame relative to the pixel of interest to a fourth constant.

One or more examples of implementations are set forth in more detail in the accompanying drawings and the description of embodiments.

LIST OF DRAWINGS

Figure 2:
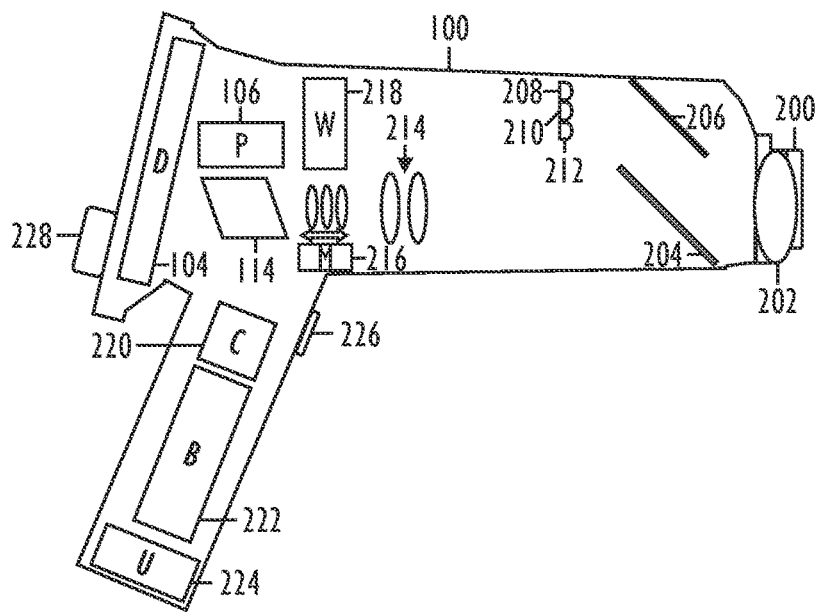
Figure 3:
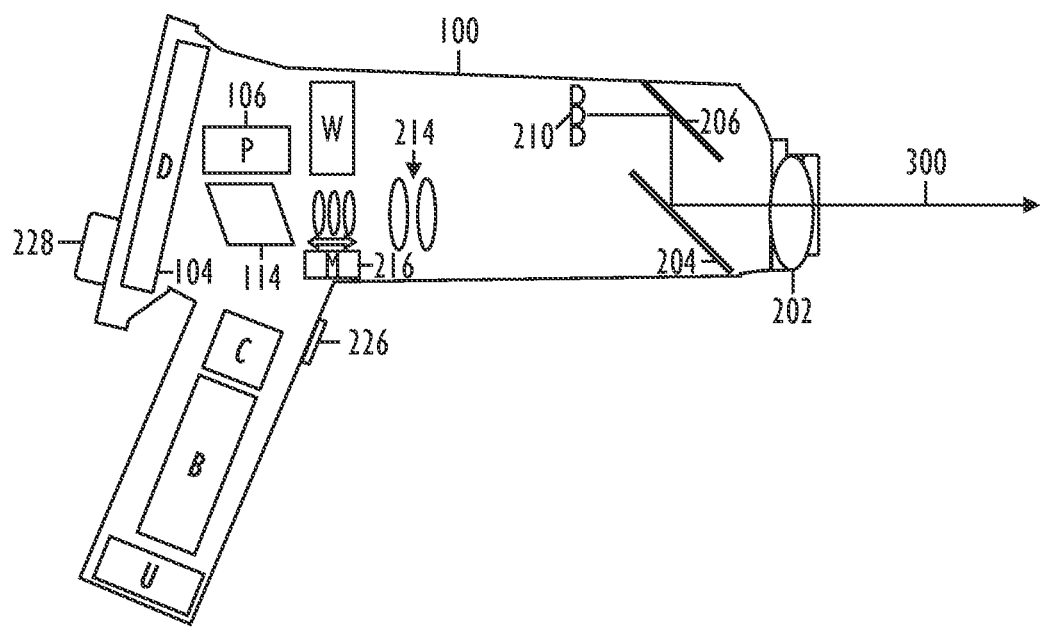
Figure 4:
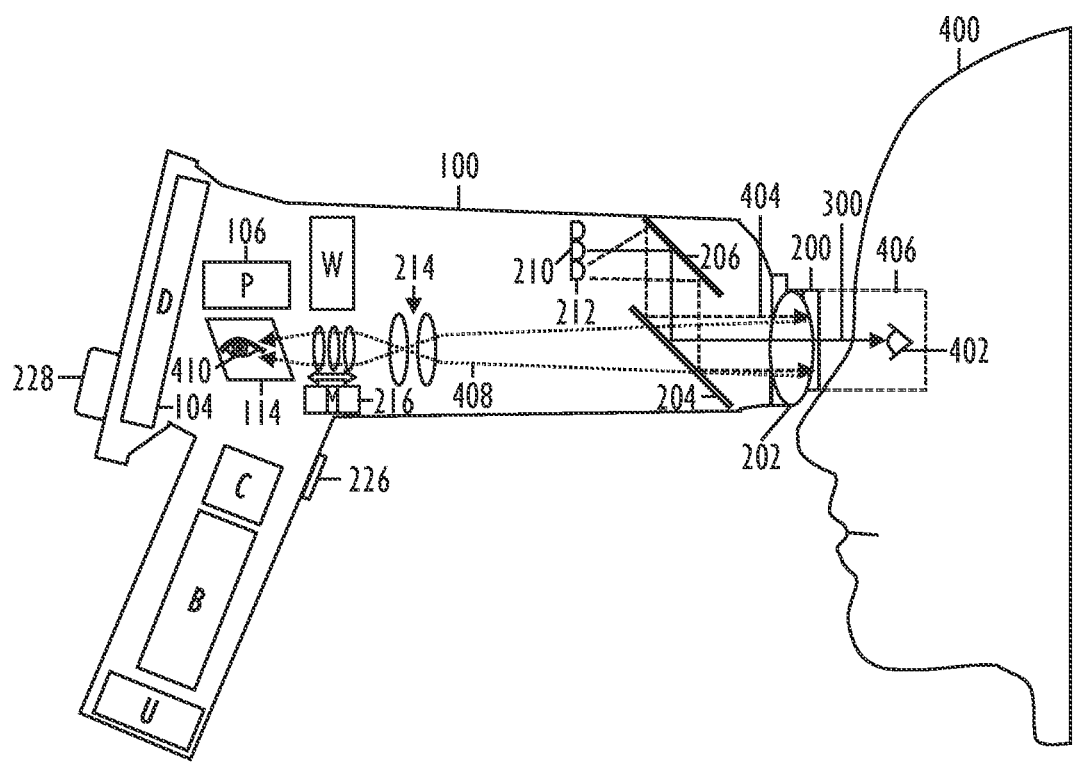
Figure 5:
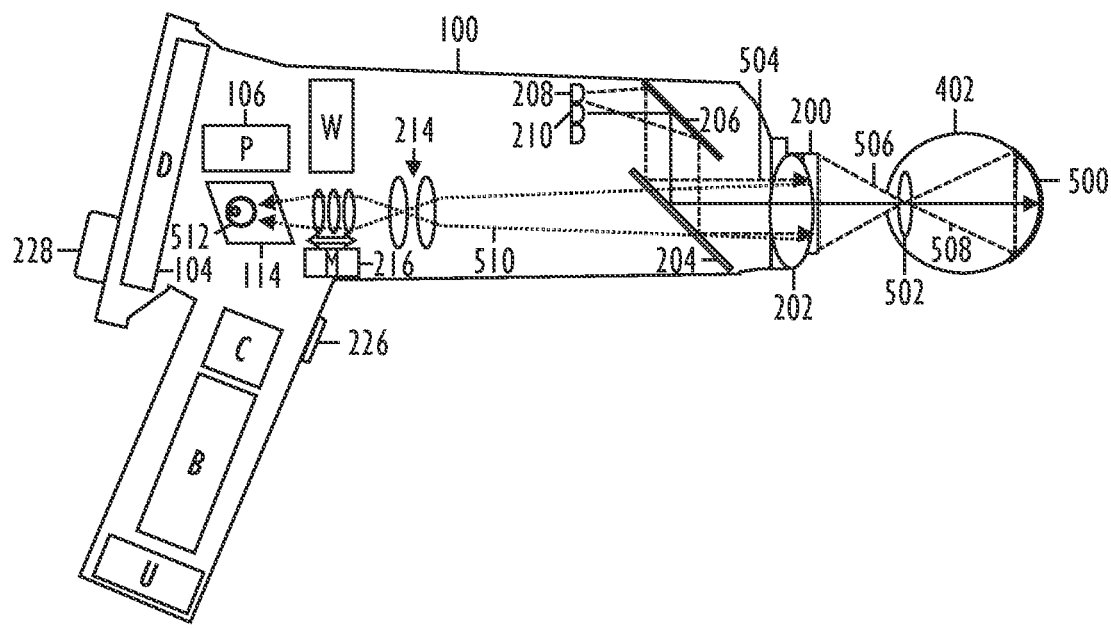
Figure 8:
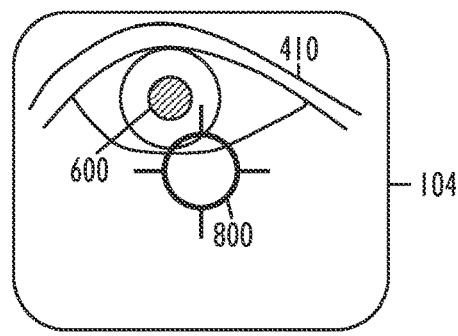
Figure 9A:
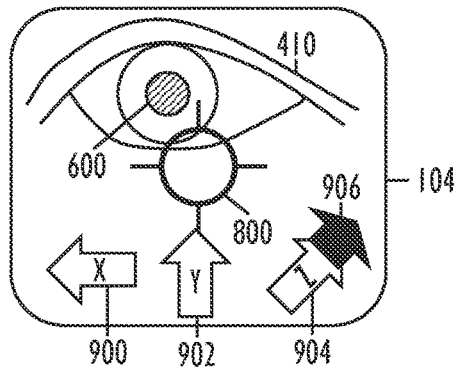
Figure 9B:
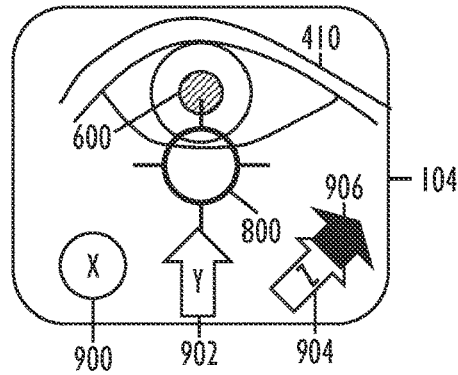
Figure 9C:
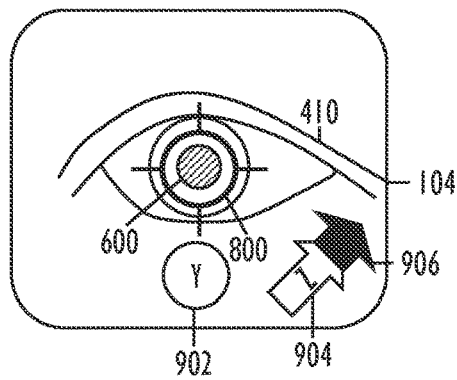
Figure 9D:
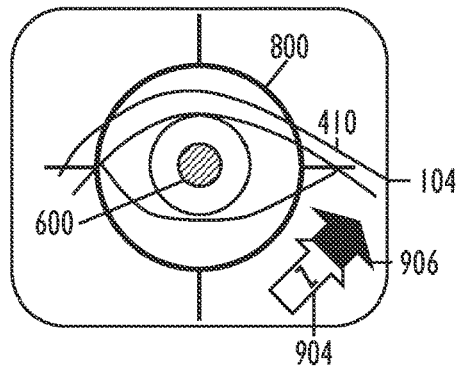
Figure 9E:
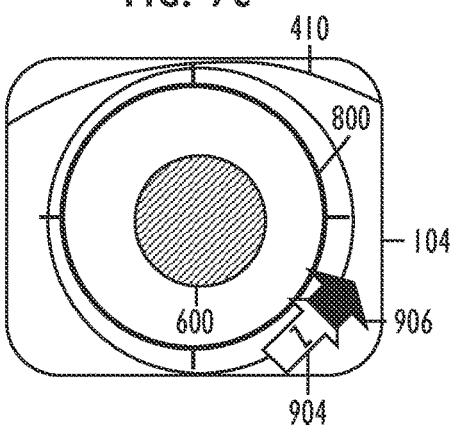
Figure 9F:
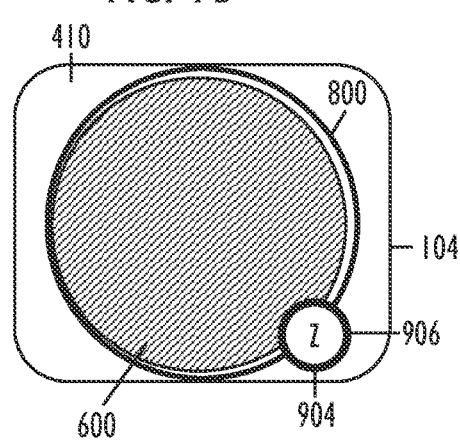
Figure 10:
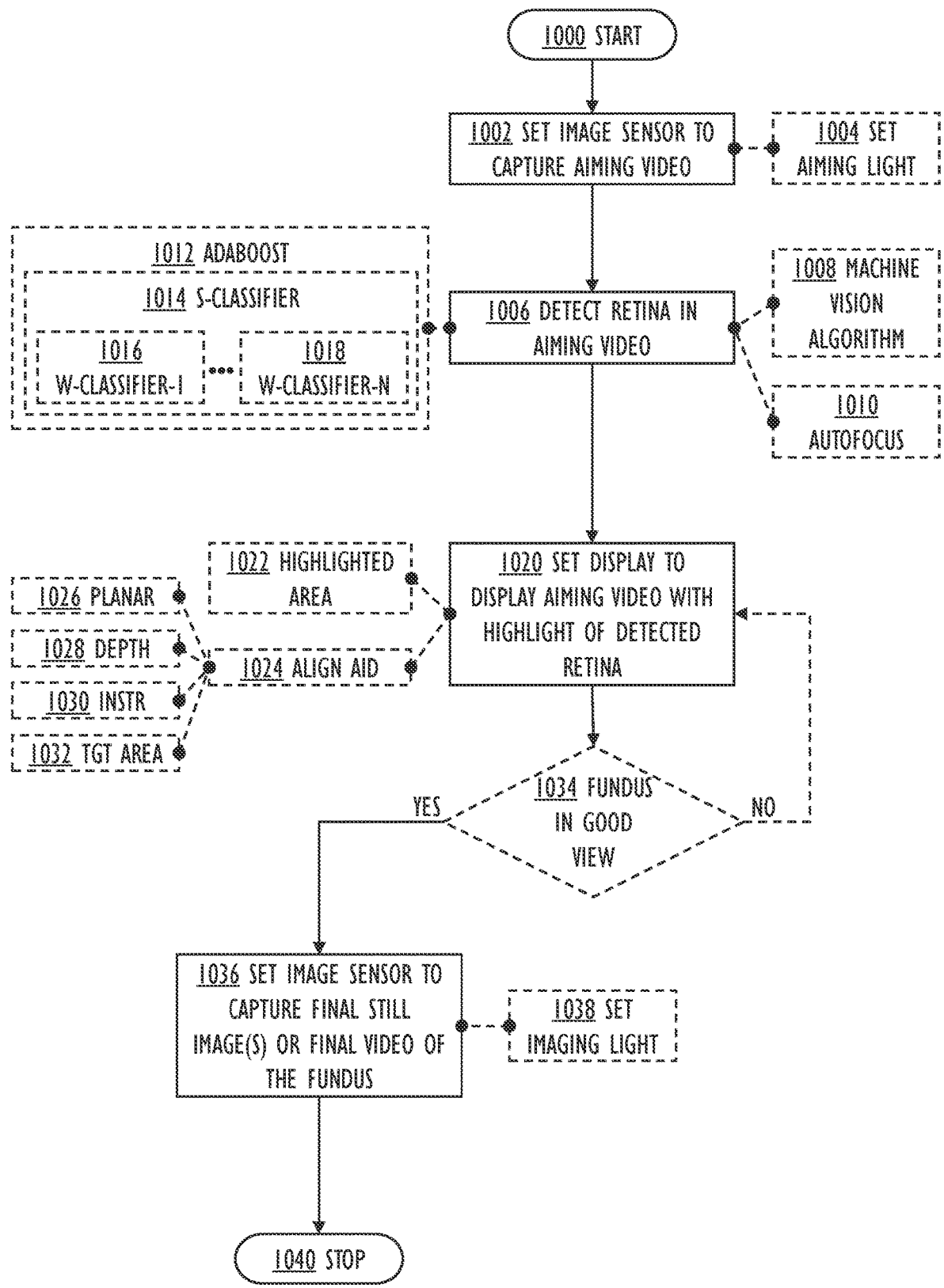

Some embodiments will now be described with reference to the accompanying drawings, in which FIG. 1 and FIG. 2 illustrate embodiments of an apparatus for imaging a fundus of an eye;

FIG. 3, FIG. 4, and FIG. 5 illustrate various light sources in the apparatus and their use in the imaging of the fundus of the eye;

FIG. 6A, FIG. 6B, FIG. 7, FIG. 8, FIG. 9A, FIG. 9B, FIG. 9C, FIG. 9D, FIG. 9E, and FIG. 9F illustrate various user interface details in the apparatus and their use in aiming of the apparatus to the fundus of the eye; and FIG. 10 is a flow chart illustrating embodiments of a method for imaging the fundus of the eye.

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Reference numbers, both in the description of the embodiments and in the claims, serve to illustrate the embodiments with reference to the drawings, without limiting it to these examples only.

The embodiments and features, if any, disclosed in the following description that do not fall under the scope of the independent claims are to be interpreted as examples useful for understanding various embodiments of the invention.

Let us study simultaneously FIG. 1 and FIG. 2, which illustrate embodiments of an apparatus 100 for imaging a fundus of an eye, and FIG. 10, which is a flow chart illustrating embodiments of a method, performed by the apparatus 100, for imaging the fundus of the eye.

The apparatus 100 for imaging the fundus of the eye comprises an optical system 116, an image sensor 114 to capture a still image or a video through the optical system 116, a user interface 102 including a display 104 to display data to a user of the apparatus 100, and one or more processors 106.

In an embodiment, the apparatus 100 is a handheld apparatus for imaging the fundus of the eye. However, the embodiments are also applicable to tabletop or stationary apparatuses for imaging the fundus of the eye.

In an embodiment, the apparatus 100 is a handheld Optomed Aurora® IQ fundus camera, but the embodiments are applicable to other models and brands with similar features.

Optomed Aurora® 100 is a modular ophthalmic camera that is designed for use in a medical environment. It is intended to capture digital images and video of the fundus of the eye and surface of the eye for documentation, screening, and consultation. It is used with interchangeable optics modules Optomed Aurora® Retinal Module and Optomed Aurora® Anterior Module. Optics modules are attached to the camera 100 with bayonet connectors. Optomed Aurora® Retinal Module is intended for non-mydriatic fundus imaging. In non-mydriatic imaging no mydriasis is needed because infrared light is used for targeting the fundus and white light is flashed when an image is taken. The pupil does not respond to the infrared light, so examination is convenient for the patient. Mydriatic drops are needed when recording a video. Mydriatic drops are also recommended when pupil diameter is small. Optomed Aurora® Retinal Module has nine internal fixation targets for the patient to fixate on during imaging. The middle fixation target provides a macula-centred image. Optomed Aurora® Anterior Module is intended for imaging the surface of the eye and the surrounding areas.

As shown in FIG. 2, the optical system 116 may comprise single lenses, 202, mirrors 204, 206, lens groups 214, motor adjustable lenses 216, but depending on the structure, also other such optical elements and also other types of optical elements used in imaging.

The image sensor 114 may be an active-pixel sensor (or CMOS sensor), but also a charge-coupled device (CCD) may be used. Optomed Aurora® 100 uses a five megapixel CMOS sensor 114.

The user interface 102 may include, besides the display 104, a touch pad (that may be integrated with the display 104 to form a touch screen), and various knobs, switches and other electrical, mechanical, or electromechanical user interface elements. As shown in FIG. 2, the user interface 102 may include a shutter button 226 and a rotary knob 228. Optomed Aurora® 100 uses a four inch TFT-LCD display with a resolution of 800×480 pixels.

The apparatus 100 may also comprise other parts, such as a WLAN module 218, which enables wireless data transfer to an external apparatus (such as a laptop or another computing device, or even a computing cloud). In addition to WLAN, captured images and recorded videos may also be transferred to the computing device via a wired connection such as an USB interface 224 when the camera 100 is placed on a charging station. The apparatus 100 may comprise one or more (rechargeable) batteries 222. The apparatus 100 may comprise an insertable SD memory card 220. The apparatus 100 may comprises numerous other parts, but as their operation is not essential for understanding the embodiments, their description will be omitted. However, some additional parts, such as leds 208, 210, 212 and a soft eye cup 200 will be explained later in relation to some optional embodiments.

In an embodiment illustrated in FIG. 1, the one or more processors 106 comprise one or more memories 110 including computer program code 112, and one or more microprocessors 108 configured to execute the computer program code 112 to cause the performance of the apparatus 100.

In an alternative embodiment, the one or more processors 106 comprise a circuitry configured to cause the performance of the apparatus 100.

A non-exhaustive list of implementation techniques for the one or more microprocessors 108 and the one or more memories 110, or the circuitry includes, but is not limited to: logic components, standard integrated circuits, application-specific integrated circuits (ASIC), system-on-a-chip (SoC), application-specific standard products (ASSP), microprocessors, microcontrollers, digital signal processors, special-purpose computer chips, field-programmable gate arrays (FPGA), and other suitable electronics structures.

The term 'memory' 110 refers to a device that is capable of storing data run-time (=working memory) or permanently (=non-volatile memory). The working memory and the non-volatile memory may be implemented by a random-access memory (RAM), dynamic RAM (DRAM), static RAM (SRAM), a flash memory (such as a NAND flash or a NOR flash), a solid state disk (SSD), PROM (programmable read-only memory), a suitable semiconductor, or any other means of implementing an electrical computer memory.

The computer program code (or software) 112 may be written by a suitable programming language (such as C, C++, assembler, or machine language, for example), and the resulting executable code may be stored in the one or more memories 110 and run by the one or more microprocessors 108. In an embodiment, the computer program code 112 may be stored in a flash memory (such as in the NAND flash) 110, and loaded by a bootloader also residing in the flash memory to the RAM 110. The computer program code implements the method/algorithm illustrated in FIG. 10. The computer program code 112 may be stored in a source code form, object code form, executable form, or in some intermediate form, but for use in the one or more microprocessors 108 it is in the executable form. There are many ways to structure the computer program code 112: the operations may be divided into modules, sub-routines, methods, classes, objects, applets, macros, etc., depending on the software design methodology and the programming language used. In modern programming environments, there are software libraries, i.e., compilations of ready-made functions, which may be utilized by the computer program code 112 for performing a wide variety of standard operations. In addition, an operating system (such as a general-purpose operating system or a real-time operating system) may provide the computer program code 112 with system services.

An embodiment provides a computer-readable medium 120 storing the computer program code 112, which, when loaded into the one or more microprocessors 108 and executed by the one or more microprocessors 108, causes the performance of the computer-implemented method/algorithm for imaging the fundus of the eye. The computer-readable medium 120 may comprise at least the following: any entity or device capable of carrying the computer program code 112 to the one or more microprocessors 108, a record medium, a computer memory, a read-only memory, an electrical carrier signal, a telecommunications signal, and a software distribution medium. In some jurisdictions, depending on the legislation and the patent practice, the computer-readable medium 120 may not be the telecommunications signal. In an embodiment, the computer-readable medium 120 is a computer-readable storage medium. In an embodiment, the computer-readable medium 120 is a non-transitory computer-readable storage medium.

Now that the basic structure of the apparatus 100 and its operating environment have been described, let us study the dynamics of the method/algorithm with reference to FIG. 10 for the main sequence and its optional embodiments. The method starts in 1000 and ends in 1040. The operations are not strictly in chronological order and some of the operations may be performed simultaneously or in an order differing from the given ones. Other functions may also be executed between the operations or within the operations and other data exchanged between the operations. Some of the operations or part of the operations may also be left out or replaced by a corresponding operation or part of the operation. It should be noted that no special order of operations is required, except where necessary due to the logical requirements for the processing order.

When imaging with the apparatus 100, the examination room should be as dim as possible. It is recommended that both a patient and a user operating the apparatus 100 are seated during the examination. It is also possible to perform the examination when the patient is lying down.

As illustrated in FIG. 3, a target light source 210 (such as a red led) shines a light 300 through the optical system 116 (such as reflected by the two mirrors 206, 204 through the lens 202.)

As illustrated in FIG. 4, the patient 400 is asked to keep the eye 402 aligned with the target light 300 and to cover the other eye but to keep the covered eye open. The user approaches the pupil of the eye 402 with the apparatus 100 and stabilizes the apparatus 100 by supporting the apparatus 100 on his/her thumb and places fingers on the forehead of the patient 400. The soft eye cup 200 is pressed firmly around the examined eye 402. The user makes micro adjustments with the supporting hand to fine tune the alignment. The pupil is approached until a reflection from the fundus of the eye 402 is seen. The right imaging distance may be about two centimetres.

It is exactly this alignment that is difficult to perform, especially for a less experienced user. The aligning may be eased with a sequence of four operations described next.

Figure 6A:
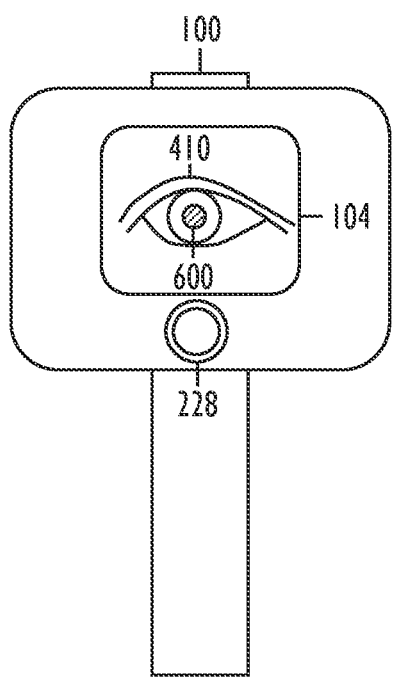
Figure 6B:
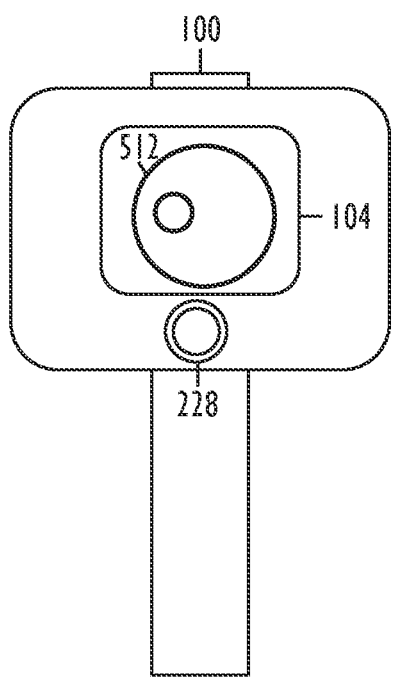

FIG. 4 and FIG. 6A illustrate an aiming phase, and FIG. 5 and FIG. 6B illustrate a capture phase.

In 1002, the image sensor 114 is set to capture an aiming video. The aiming is illustrated in the FIG. 4: the image sensor 114 captures the aiming video 410 through 408 the optical system 116 (comprising the lenses 202, 214, 216).

In 1006, a retina of the eye 402 is detected in the aiming video. As shown in FIG. 5, the fundus 500 is imaged through the pupil 502.

In 1020, the display 104 is set to display the aiming video with a highlight of the detected retina. As shown in FIG. 6A, the aiming video 410 illustrates the vicinity of the eye 402, and the detected retina is shown with a highlight 600 on the display 104.

In an embodiment of 1020, the display 104 is set to highlight the detected retina in the aiming video as a highlighted area 600, 1022 marking the detected retina. The highlighted area 600, 1022 may be coloured with a suitable colour that is clearly distinguishable from the surrounding area (such as the iris of the eye, the sclera of the eye, and the skin surrounding the eye). The highlighted area 600, 1022 may also be shown with a clearly visible borderline around the area, or with a suitable pattern fill covering the area.

In 1036, the image sensor 114 is set to capture one or more final still images of the fundus 500 or a final video of the fundus 500. The capture is illustrated in the FIG. 5: the image sensor 114 captures the final still image(s) 512 or the final video 512 through 510 the optical system 116 (comprising the lenses 202, 214, 216).

In an embodiment, detecting the retina in 1006 comprises using 1008 a machine vision algorithm trained with images of eyes with annotated fundi.

In an embodiment, detecting the retina in 1006 comprises using 1012 an Adaptive Boosting, AdaBoost, statistical classification meta-algorithm or one of its variants, which construct a strong classifier 1014 by combining results of a sequence of weak classifiers 1016, 1018.

In an embodiment, a probability of a pixel of interest in a single frame of the aiming video belonging to the retina is determined, by the weak classifiers 1016, 1018, by comparing either an average luminosity of an area in the single frame relative to the pixel of interest to a first constant, or a difference of averages of luminosities of two areas in the single frame relative to the pixel of interest to a second constant.

In an embodiment, also one or more results of comparisons are used, by the weak classifiers 1016, 1018, from previous weak classifiers in the sequence of the classifiers to improve the accuracy of a next weak classifier in the sequence of the classifiers.

In an embodiment, also average probabilities of pixels in areas in the single frame belonging to the retina are compared by the weak classifiers 1016, 1018 as determined by an already executed weak classifier as follows: comparing either an average probability of an area in the single frame relative to the pixel of interest to a third constant, or a difference of averages of probabilities of two areas in the single frame relative to the pixel of interest to a fourth constant.

Recognizing objects, such as faces, pedestrians or in our case retinas in the image has for decades been regarded as a machine learning task: the developer collects representative images and annotates the objects to be detected in them. A machine learning algorithm then uses these training examples to detect the objects of interest in yet unseen images. Since these unseen images may not exist in the training examples, the machine learning algorithm must do its best to generalize the information included in the training examples.

While "deep learning" of artificial neural networks has without a doubt shown the most accurate image detection and segmentation results for the past decade, they are computationally expensive to a degree that they may have to be excluded from such a small and battery-powered device 100. Therefore, for example, the task of detecting a human face in an image and finding the smallest rectangle containing the whole face is still typically performed with "classic" machine learning algorithms predating the success of deep learning. The best known of such algorithms is called the Viola-Jones face detection algorithm, and it is based on the more general idea of the AdaBoost 1012, which builds an accurate "strong" machine learning algorithm 1014 by employing a sequence of simpler and more inaccurate "weak" machine learning algorithms 1016, 1018 and performing a weighted voting or weighted summation of the weak learners' results. The rich mathematical foundation of AdaBoost and its dozens of variants have been well documented in the scientific literature.

Practitioners of the AdaBoost use most commonly decision trees of various kinds as the weak learners 1016, 1018.

The simplest possible decision tree, a decision stub, performs a simple comparison of a feature value to a decision boundary value. While this, combined with a good choice of image features as in the Viola-Jones algorithm, has been shown to perform well in face detection tasks, a more difficult image detection task may require prohibitively many weak learners thereby respectively slowing down the image detector. On the other extreme one may be tempted to build a very deep decision tree, possibly one where each leaf corresponds to a single training example. While such a decision tree would indeed be fully accurate on training data, it would also generalize poorly to other inputs than the given training examples. Practitioners therefore choose an a priori maximum height, say six, for the decision tree in their attempt to find a compromise between the higher performance of fewer weak learners 1016, 1018 and good generalization characteristics of more numerous weak learners 1016, 1018.

Decision trees contain several aspects we consider suboptimal: Firstly, following the then- and else-branches of the decision is highly likely to cause pipeline hazards in the processor resulting in both excessive energy (battery) consumption and a significant performance reduction. Secondly, a decision tree of any significant height will result in an exponential increase in program size. Our contributions include increasing the accuracy of decision stubs with the ability to refer to the result of earlier (not necessarily immediately preceding) decision stubs. In other words, if the N'th decision stump is implemented conventionally in pseudo-code as $cmp_N = 1$ if then-branch taken in N'th decision stump, else 0

$sum\mathrel{+}= weight\_table_N[cmp_N]$ where sum represents the weighted sum of the AdaBoost or its variants, then we propose to use a reasonable number, here five, of earlier comparisons for example as follows:

$cmp_N = 1$ if then-branch taken in N'th decision stump, else 0

$sum\mathrel{+}= weight\_table_N[cmp_N][cmp_{N-a}][cmp_{N-b}][cmp_{N-c}][cmp_{N-d}]$ where the distinct positive values a to d refer to the distances to the previous comparison from N. Note that even though the weight_table grows similarly exponentially as caused by the depth of the decision tree discussed earlier, the table contains typically smallish integer or floating-point values and consumes overall significantly less memory than a decision tree would. Note also that this added functionality does not entail any more branching and pipeline stalls causes by branching. Furthermore, note that in a practical application the list of values $cmp_N$ could be implemented cheaply using a bit vector.

For a while, consider the retina detection algorithm working by applying the AdaBoosted classifier in turn for each pixel ("pixel of interest") in a reduced resolution grayscale aiming image of the fundus camera 100. The Viola-Jones algorithm for face detection uses "Haar-like features" as the values to compare in the conditions of the weak classifiers. A Haar-like feature considers adjacent rectangular regions of equal size at a specific location relative to the pixel of interest, sums up the pixel luminosities in each region and calculates the difference between these sums. The difference is then compared to a boundary value to yield the weak classifier. Haar-like features have the benefit of being efficiently computable by precomputing an "integral image" (also known as "summed-area table") for the image. Some systems use also Haar-like features tilted by 45 degrees, with corresponding precomputed integral images.

We have found that at least for retina detection strict Haar-like features result in somewhat too inaccurate weak classifiers. Particularly, we have found it beneficial to lift the limitation that the rectangles, or tilted rectangles, must be adjacent and that they must be of equal size. This choice allows a well-chosen weak learner to detect regions inside other regions, such as the darker pupil and iris inside the white sclera, or the reflection of an infrared light of an aiming light source 212 (explained later) inside the region of the pupil.

Consequently, instead of using the sum of pixel luminosities we use the average of the pixel luminosities in the compared rectangles. At first this would seem to imply a costly floating-point division, but in fact we may multiply the compared averages to the lowest common multiple of the sizes of the rectangles. Furthermore, because in our implementation these multipliers are compile-time constants in the retina detector's source code, the compiler will often find strength-reduction optimizations resulting in negligible computational overhead.

The retina is a relatively textureless object and may in the aiming image easily be confused with, say, the cheek or forehead of the patient 400. However, if the aiming image (or video) 410 contains, for example, the optic disc, then one is certain that the adjacent area is indeed of the retina, and conversely, if the image contains the nose, eyebrows, or members of the outer eye, then indicating a retina detection is premature. In other words, given a pixel of interest in a textureless surrounding, it being part of the retina correlates most strongly with whether nearby pixels have been determined to belong to the retina.

The above observation has led us to restructure the overall retina detection algorithm as follows:

1. Downscale the aiming image to a suitable resolution.
2. Compute integral images for a fast computation of the average luminosity of rectangular and possibly tilted rectangular areas.
3. For each pixel in the image, execute, say, k first weak classifiers 1016, 1018 resulting in a sum-value for each of the pixels of interest. These first weak classifiers 1016, 1018 may only use pixel and average rectangle luminosities.
4. Construct a two-dimensional array of the pixelwise sum-values. This array is of identical dimensions as the downscaled aiming image and may thus be treated as a second image to be used by weak classifiers 1016, 1018. To facilitate this, compute also the integral images for this "sum-image".
5. For each pixel in the image, execute the next, say, j weak classifiers 1016, 1018 updating the sum-values for each pixel. These weak classifiers 1016, 1018 may use not only features found in the downscaled aiming image, but also in the sum-image.
6. If a sufficient accuracy of retina detection has been found, as in original the AdaBoost, the sign of each value in the sum-image indicates whether the pixel is part of the retina or something else. Alternatively, repeat these steps 4-6 for the next weak classifiers 1106, 1018.

In practice we have found that the accuracy or the performance of the retina detection algorithm depend little on the exact choice of k and j above. Overly small values result in some waste of performance to needlessly recomputing the integral of sum-images, and too large values of k and j result in needlessly weak weak classifiers 1016, 1018. We typically use values around five fork and j.

Next, let us study the user interface 102, especially the display 104 during the aiming and capture in more detail.

Figure 7:
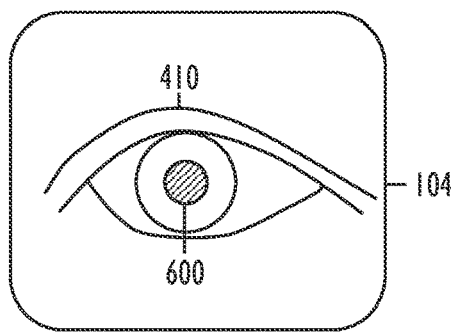

FIG. 7 illustrates the display 104 showing the aiming video 410, wherein the detected retina is shown with the highlight 600.

FIG. 8 illustrates an embodiment, wherein the display 104 is set to display the aiming video 410 with an align aid 800, 1024 related to a position of the highlight 600 of the detected retina on the display 104. The align aid 800 may be a sight symbol as illustrated in FIG. 8, but it may also be another kind of align aid, such as a transparent overlay symbol in the form of the pupil. In an embodiment, the display 104 is set to display the align aid 1024 with an aiming target area 1032 in a middle of the display 104 and in relation to the highlight 600 of the detected retina in the display 104 while the image sensor 114 is capturing the aiming video 410.

The idea is that the user will move the apparatus 100 so that the align aid 800 becomes overlapped with the highlight 600 of the detected retina. To achieve the overlapping, the user may have to cause a movement of the optical system 116 in a planar direction (such as in x and y directions along the surface of the face and iris) and in a depth direction (such as in z direction towards the iris or away from the iris).

FIG. 9A illustrates an embodiment, wherein the display 104 is set to display the align aid 800, 1024 with a planar indicator 900, 902, 1026 of the x and y direction alignment of the highlight 600 of the detected retina in the display 104, and a depth indicator 904, 1028 of the z direction alignment of the apparatus 100 in relation to the highlight 600 of the detected retina in the display 104. The display 104 is also set to display the align aid 800, 1024 with an instruction 906, 1030 instructing the user to move the optical system 116 nearer to the eye or further off the eye. Note that besides the arrow symbols 900, 902, 904, 906 other kinds of symbols may to used to indicate the various alignments and instructions.

Note also that the display 104 may also be set to display the align aid 800, 1024 with an instruction instructing the user to move the optical system 116 in the x and/or y direction, this is actually shown in FIG. 9A so that the x direction planar indicator 900 shows with the direction of the arrow that the optical system 116 should be moved to the left so that the align aid 800 becomes aligned in the x direction with the highlight 600. Also, the y direction planar indicator 902 shows with the direction of the arrow that the optical system 116 should be moved to the up so that the align aid 800 becomes aligned in the y direction with the highlight 600.

In FIG. 9B, the x direction alignment has been reached, and the x direction planar indicator 900 is changed to a round symbol.

In FIG. 9C, the x direction planar is no more shown, and also the y direction alignment has been reached, and the y direction planar indicator 902 is changed to a round symbol.

In FIG. 9D, as the x and y direction alignments have been achieved no planar indicators 900, 902 are shown, but the z direction (or depth) indicator 904 is still shown with the instruction 906. FIG. 9D also illustrates that as the user has moved the optical system 116 nearer, the align aid 800 is also enlarged.

In FIG. 9E, the instruction 906 still instructs to move closer, and the align aid 800 has also grown larger.

Finally, in FIG. 9F, the highlight 600 of the detected retina fills the align aid 800. As the align aid 800 is now of the correct size filling the display 104, the depth indicator 904 is changed to a round symbol, and the instruction 906 highlights the indicator 904, thereby signalling that the alignment is now perfect, and the final still image(s) or the final video may be captured. Note that the z direction (or depth indicator) 904 may pause in this full view, so that the final still image or the final video may be captured, but after this, it may further instruct the user to move the optical system nearer 116 to take more final still images or additional final video. This may be required as there may still be reflections caused by the retina in the full view still images/video.

In an embodiment, the sequence of operations in FIG. 10 may be augmented by an optional test in 1034. The test may check whether the detected retina fulfils a predetermined condition, such as whether the detected retina fills the align aid as shown in FIG. 9, or whether the detected retina in some other way indicates that an adequately good image or video of the fundus 500 may be captured. If the detected retina fulfils a predetermined condition (the test in 1034 evaluates "YES"), the image sensor 114 is set in 1036 to capture the one or more final still images 512 or the final video 512, or else (the test in 1034 evaluates "NO"), the aiming video 410 is continued to be captured. Besides such automatic capture, the user may of course capture the final still image(s) or video by operating an appropriate user interface control, such as pressing the shutter button 226.

In an embodiment, the optical system 116 is set to autofocus 1010 on the detected retina while the image sensor 114 is capturing the aiming video 410. The autofocus range may be from −15 to +10 dioptres, for example. If the refractive error (hyperopia or myopia) of the patient is known, the dioptre value may also be manually entered with an appropriate user interface control, such as a touch screen 104 and/or the rotary button 228. In an embodiment, the apparatus 100 comprises a mechanism 200, 216 to adjust the optical system 116 in relation to the eye and the fundus of the eye while the image sensor 114 is capturing the aiming video 410 and the one or more final still images 512 or the final video 512. The mechanism may comprise the soft eye cup 200, with which the distance and direction of the foremost lens 202 may be adjusted in relation to the eye 402. The mechanism may also comprise an adjustment within the optical system 116, such as the motor adjustable lenses 216, with which the focus may be adjusted.

In an embodiment, the apparatus 100 comprises an aiming light source 212 to illuminate 404, 406 the eye 402 through the optical system 116, and an imaging light source 208 to illuminate 504, 506, 508 the fundus 500 through the optical system 116. As shown in FIG. 4 and FIG. 5, the light sources 208, 212 may be alternatively lit and their light directed via the mirrors 206, 204 through the foremost lens 202. The one or more processors 106 cause setting 1004 of the aiming light source 212 to illuminate 406 the eye 402 while the image sensor 114 is capturing the aiming video 410, and setting 1038 of the imaging light source 208 to illuminate 508 the fundus 500 while the image sensor 114 is capturing the one or more final still images 512 or the final video 512. In an embodiment, the aiming light source (212) comprises an infrared (IR) light emitting diode (LED), and the imaging light source 208 comprises a white light emitting diode (LED). The infrared led does not cause discomfort during the (possibly relatively long) aiming, whereas the white light led provides neutral lighting during the (possibly relatively brief) capture. The infrared led may be a near infrared (NIR) led.

Even though the invention has been described with reference to one or more embodiments according to the accompanying drawings, it is clear that the invention is not restricted thereto but can be modified in several ways within the scope of the appended claims. All words and expressions should be interpreted broadly, and they are intended to illustrate, not to restrict, the embodiments. It will be obvious to a person skilled in the art that, as technology advances, the inventive concept can be implemented in various ways.

The invention claimed is:

1. An apparatus configured to image a fundus of an eye, comprising:
    an optical system;
    an image sensor configured to capture a still image or a video through the optical system;
    a user interface including a display configured to display data to a user of the apparatus;
    one or more processors configured to cause performance of at least the following:
        setting the image sensor to capture an aiming video;
        detecting a retina of the eye in the aiming video, wherein detecting the retina comprises using an Adaptive Boosting, AdaBoost, statistical classification meta-algorithm or one of its variants, which constructs a strong classifier by combining results of a sequence of weak classifiers;
        setting the display to display the aiming video with a highlight of the detected retina;
        setting the image sensor to capture one or more final still images of the fundus or a final video of the fundus;
        using, by the weak classifiers, also one or more results of comparisons from previous weak classifiers in the sequence of the classifiers to improve the accuracy of a next weak classifier in the sequence of the classifiers; and
        comparing, by the weak classifiers, also average probabilities of pixels in areas in the single frame belonging to the retina as determined by an already executed weak classifier as follows: comparing either an average probability of an area in the single frame relative to the pixel of interest to a third constant, or a difference of averages of probabilities of two areas in the single frame relative to the pixel of interest to a fourth constant.

2. The apparatus of claim 1, wherein detecting the retina comprises using a machine vision algorithm trained with images of eyes with annotated fundi.

3. The apparatus of claim 1, wherein the one or more processors cause performance of at least the following:
    determining, by the weak classifiers, a probability of a pixel of interest in a single frame of the aiming video belonging to the retina by comparing either an average luminosity of an area in the single frame relative to the pixel of interest to a first constant, or a difference of averages of luminosities of two areas in the single frame relative to the pixel of interest to a second constant.

4. The apparatus of claim 1, wherein the one or more processors cause performance of at least the following:
    setting the display to highlight the detected retina in the aiming video as a highlighted area marking the detected retina.

5. The apparatus of claim 1, wherein the one or more processors cause performance of at least the following:
    setting the display to display the aiming video with an align aid related to a position of the highlight detected retina on the display.

6. The apparatus of claim 5, wherein the one or more processors cause performance of at least the following:
    setting the display to display the align aid with a planar indicator of the x and y direction alignment of the highlight of the detected retina in the display, and a depth indicator of the z direction alignment of the apparatus in relation to the highlight of the detected retina in the display; and
    setting the display to display the align aid with an instruction instructing the user to move the optical system nearer to the eye or further off the eye.

7. The apparatus of claim 5, wherein the one or more processors cause performance of at least the following:
    setting the display to display the align aid with an aiming target area in a middle of the display and in relation to the highlight of the detected retina in the display while the image sensor is capturing the aiming video.

8. The apparatus of claim 1, wherein the one or more processors cause performance of at least the following:
    setting the optical system to autofocus on the detected retina while the image sensor is capturing the aiming video.

9. The apparatus of claim 1, wherein the one or more processors cause performance of at least the following:
    if the detected retina fulfils a predetermined condition, setting the image sensor to capture the one or more final still images or the final video, or else continuing to capture the aiming video.

10. The apparatus of claim 1, further comprising:
    an aiming light source configured to illuminate the eye through the optical system; and
    an imaging light source configured to illuminate the fundus through the optical system,
    wherein the one or more processors cause performance of at least the following:
        setting the aiming light source to illuminate the eye while the image sensor is capturing the aiming video; and
        setting the imaging light source to illuminate the fundus while the image sensor is capturing the one or more final still images or the final video.

11. The apparatus of claim 10, wherein the aiming light source comprises an infrared light emitting diode, and the imaging light source comprises a white light emitting diode.

12. The apparatus of claim 1, further comprising:
    a mechanism configured to adjust the optical system in relation to the eye and the fundus of the eye while the image sensor is capturing the aiming video.

13. A method for imaging a fundus of an eye comprising:
    setting an image sensor to capture an aiming video through an optical system;
    detecting a retina of the eye in the aiming video, wherein detecting the retina comprises using an Adaptive Boosting, AdaBoost, statistical classification meta-algorithm or one of its variants, which constructs a strong classifier by combining results of a sequence of weak classifiers;
    setting a display to display the aiming video with a highlight of the detected retina;
    setting the image sensor to capture one or more final still images of the fundus or a final video of the fundus through the optical system;
    using, by the weak classifiers, also one or more results of comparisons from previous weak classifiers in the sequence of the classifiers to improve the accuracy of a next weak classifier in the sequence of the classifiers; and comparing, by the weak classifiers, also average probabilities of pixels in areas in the single frame belonging to the retina as determined by an already executed weak classifier as follows: comparing either an average probability of an area in the single frame relative to the pixel of interest to a third constant, or a difference of averages of probabilities of two areas in the single frame relative to the pixel of interest to a fourth constant.

14. The method of claim 13, further comprising determining, by the weak classifiers, a probability of a pixel of interest in a single frame of the aiming video belonging to the retina by comparing either an average luminosity of an area in the single frame relative to the pixel of interest to a first constant, or a difference of averages of luminosities of two areas in the single frame relative to the pixel of interest to a second constant.

15. The method of claim 13, further comprising setting the display to display the aiming video with an align aid related to a position of the highlight detected retina on the display.

16. The method of claim 15, further comprising:
setting the display to display the align aid with a planar indicator of the x and y direction alignment of the highlight of the detected retina in the display, and a depth indicator of the z direction alignment optical system in relation to the highlight of the detected retina in the display; and
setting the display to display the align aid with an instruction instructing the user to move the optical system nearer to the eye or further off the eye.

17. The method of claim 15, further comprising setting the display to display the align aid with an aiming target area in a middle of the display and in relation to the highlight of the detected retina in the display while the image sensor is capturing the aiming video.

18. The method of claim 13, further comprising setting the optical system to autofocus on the detected retina while the image sensor is capturing the aiming video.

19. The method of claim 13, further comprising:
setting an aiming light source to illuminate the eye while the image sensor is capturing the aiming video; and
setting an imaging light source to illuminate the fundus while the image sensor is capturing the one or more final still images or the final video.

20. The method of claim 19, wherein the aiming light source comprises an infrared light emitting diode, and the imaging light source comprises a white light emitting diode.

* * * * *